(12) United States Patent  
Eckerbom

(10) Patent No.: US 7,235,054 B2  
(45) Date of Patent: Jun. 26, 2007

(54) MEASURING HEAD FOR A GAS ANALYSER

(75) Inventor: Anders Eckerbom, Vaxholm (SE)

(73) Assignee: Phase-In AB, Stockholm (SE)

( * ) Notice: Subject to any disclaimer, the term of this patent is extended or adjusted under 35 U.S.C. 154(b) by 0 days.

(21) Appl. No.: 10/494,273

(22) PCT Filed: Oct. 25, 2002

(86) PCT No.: PCT/SE02/01946

§ 371 (c)(1),
(2), (4) Date: Apr. 30, 2004

(87) PCT Pub. No.: WO03/060490

PCT Pub. Date: Jul. 24, 2003

(65) Prior Publication Data

US 2004/0267151 A1    Dec. 30, 2004

(30) Foreign Application Priority Data

Oct. 30, 2001   (SE) .................................... 0103599

(51) Int. Cl.
- *A61B 5/08* (2006.01)
- *G01N 1/22* (2006.01)
- *G01N 31/00* (2006.01)
- *G01N 33/497* (2006.01)

(52) U.S. Cl. ........................ 600/532; 73/23.3; 422/84

(58) Field of Classification Search ................ 600/532; 73/23.3; 422/84

See application file for complete search history.

(56) References Cited

U.S. PATENT DOCUMENTS

| 5,445,160 | A | 8/1995 | Culver et al. |
| 5,464,982 | A | 11/1995 | Drucker et al. |
| 6,039,697 | A | 3/2000 | Wilke et al. |
| 6,267,928 | B1* | 7/2001 | Yamamori et al. ............ 422/84 |
| 6,277,081 | B1 | 8/2001 | Susi et al. |
| 6,475,158 | B1* | 11/2002 | Orr et al. .................... 600/531 |
| 6,632,402 | B2* | 10/2003 | Blazewicz et al. ............ 422/84 |
| 6,811,751 | B1* | 11/2004 | Olsson et al. ................. 422/84 |
| 2001/0031224 | A1 | 10/2001 | Labuda et al. |
| 2002/0029003 | A1* | 3/2002 | Mace et al. ................. 600/532 |

FOREIGN PATENT DOCUMENTS

| EP | 0 895 077 | 2/1999 |
| EP | 1 112 716 | 7/2001 |

* cited by examiner

*Primary Examiner*—Robert L. Nasser
(74) *Attorney, Agent, or Firm*—Young & Thompson

(57) ABSTRACT

A measuring head for the analysis of respiratory gases to and from a patient connected to a respirator, includes an aperture (7) which is intended to be placed over an adapter (2) through which respiratory gases flow. The measuring head (1) has a light transmitter (9) which includes an IR-emitter (12) on one side of the aperture (7) and a light receiver (10) which includes an IR-detector on the other side of the aperture (7). The measuring head (1) also includes a signal processing unit (20) necessary for the gas analysis.

13 Claims, 2 Drawing Sheets

MEASURING HEAD FOR A GAS ANALYSER

BACKGROUND OF THE INVENTION

The present invention relates to a measuring head for use in the analysis of respiratory gases to and from a patient-connected respirator for breathing assistance.

DESCRIPTION OF RELATED ART

With regard to gas analysis carried out in connection with respiratory care, a distinction is made between two principle types of gas analysers, i.e. between lateral flow measuring analysers and main flow measuring analysers. The lateral flow measuring analysers take a minor sample flow from the respiratory circuit of a patient to an adjacent instrument in which the actual gas analysis takes place, whereas the main flow measuring analysers calculate the gas concentrations directly in the respiratory circuit of the patient. The main flow measuring analyser is normally placed at close as possible to the patient's mouth or trachea, for reasons of accuracy.

The main flow measuring analysers can be made less expensive, smaller, more energy-lean and more responsive than the lateral flow measuring analysers, since the need for sample flow handling (pumps, hoses, etc.) is obviated. Consequently, the main flow measuring gas analysers are preferred to the lateral flow measuring analysers.

Various requirements for gas analyses exist in health care. For example, it is sufficient to monitor breathing of a patient with a simple carbon dioxide analysis in the case of emergency care, whereas it is often desired to measure and monitor a greater number of patient gases, such as carbon dioxide, oxygen gas, nitrous oxide and one or more of the anaesthesia agents Halothan, Enfluran, Isofluran, Sevofluran and Desfluran in the case of patient anaesthesia.

For reasons of a technical nature, it has been difficult to develop main flow measuring patient-gas analysers other than for carbon dioxide. Although such analysers have found a broad use spectrum in emergency care in particular, the use of lateral flow measuring analysers has been referred to in other care aspects, such as intensive care and anaesthesia, for instance, due to the occurrence of technical problems, primarily related to moisture and bacteria in the patient's respiratory circuit. Moreover, it has been difficult to develop sufficiently small main flow measuring gas-flow analysers. As a result, it has been necessary to divide the analyser into a fixed part, which is normally mounted in a table instrument, and a movable sensor part which is placed close to the patient's mouth or trachea. Such solutions have made the analyser more expensive, in addition to making service more troublesome and requiring the two parts to be calibrated with respect to one another.

Respiratory gases can be analysed in accordance with different measuring principles. The most common method of gas analysis, however, is through the medium of non-dispersive spectroscopy. This measuring principle is based on the fact that many gases absorb infrared energy at a wavelength specific to the substance concerned. Main flow measuring gas analysers based on non-dispersive spectroscopy measure light absorption at specific wavelengths directly in the patient's respiratory circuit. An earlier known design of one such gas analyser is described in WO91/18279 A1, for instance. In the case of this gas analyser, a broadband infrared light beam is allowed to pass through the patient's respiratory circuit.

The light beam is then divided by a beam splitter into two beams, which are registered by two separate detectors provided with optical bandpass filters having mutually different centre wavelengths. One detector is used to calculate the intensity of the light beam at the absorption wavelength of the analysis substance, whereas the other detector is used to calculate a measurement of the reference intensity of the light beam at a wavelength different from the absorption wavelength of the analysis substance. This type of gas analyser is well suited for the analysis of individual gases, such as carbon dioxide, for instance. However, intensity losses in the beam splitter and the size of the beam splitter make this type of analyser unsuitable for the multigas analysis based on main flow.

Unfortunately, oxygen gas exhibits no marked absorption within the infrared range and, in respect of oxygen gas analysis, there are normally used fuel cells or analysers that utilise the paramagnetic properties of oxygen gas. These latter solutions are highly "shock"-sensitive, which makes them unsuitable for main flow measuring analysis.

Fuel cells are comprised of a gold cathode and a lead anode surrounded by an electrolyte protected by a membrane through which oxygen-gas diffuses into the cell. The current generated by the cell is directly proportional to the partial pressure of the oxygen gas. The response time of the cell is dependent on the design of the membrane and its thickness, and also to the extent to which the gas yield is permitted to take place nearest the membrane. However, response times are normally in the magnitude of from one to ten seconds. Response times of such long duration have made it difficult to use fuel cells for registration of oxygen gas that is dissolved during main flow measuring gas analysis.

A gas analyser measuring head is known from U.S. Pat. No. 5,464,982 for example. The known measuring head includes an infrared light emitter on one side of an aperture and an infrared light receiver on the other side of the aperture. Measurement signals are led from the measuring head to a signal evaluating device, which may be arranged in a personal computer (PC) or the like that includes a program for processing the signal values obtained from the measuring head.

SUMMARY OF THE INVENTION

Accordingly, the object of the present invention is to provide a novel arrangement with which all of the gases occurring in respiratory care can be analysed by a main flow measuring process in a sensor that is placed totally in the close proximity of the patient's mouth or trachea and that can be readily adapted to different care systems, e.g. to personal computers, monitoring instruments, without needing to be provided with special electronics or to be adapted mechanically to the measuring head used, and also to enable the measuring heads to be readily switched between different care systems in the absence of separate calibration systems or calibration procedures.

These objects are achieved with an inventive measuring head that also includes a signal processing unit necessary for gas analysis.

BRIEF DESCRIPTION OF THE DRAWINGS

The invention will now be described in more detail with reference to a non-limiting embodiment and also with reference to the accompanying drawings, in which.

DESCRIPTION OF THE PREFERRED EMBODIMENTS

Figure 1:
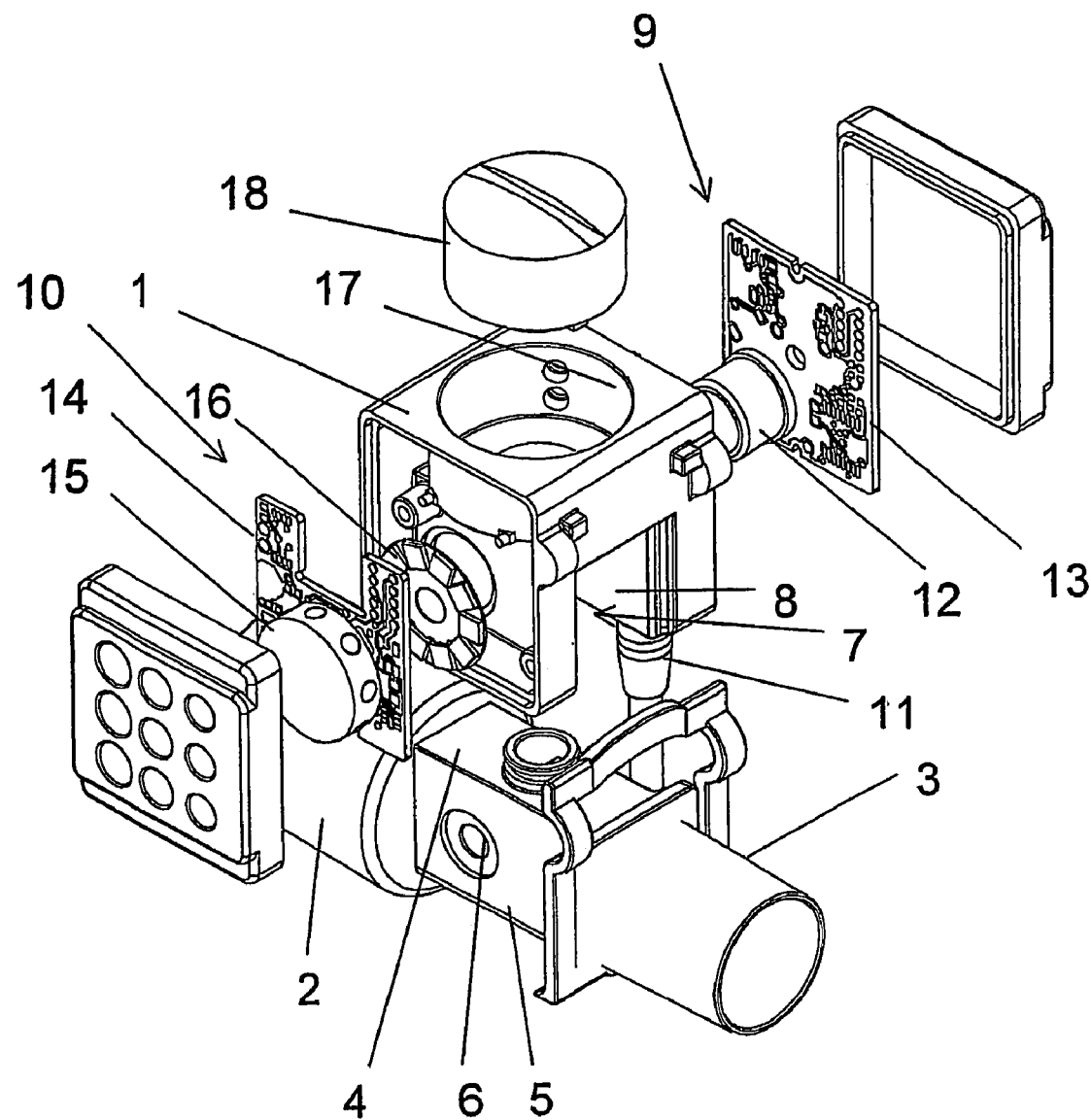
FIG. 1 is an exploded schematic view of an inventive measuring head which is intended to be fitted to an adapter through which respiratory gases are passed to the patient.

Thus, FIG. 1 shows a gas analyser measuring head 1 which is intended to be fitted onto an adapter 2. The adapter can be seen mainly as an elongate tube comprised, for instance, of plastic material. The adapter 2 carries at one end a connector for connection to a hose that leads to the patient and at the other end a connector 3 for connection to a respirator or the like. The adapter includes between the two connectors a central portion 4 that is designed to accommodate the measuring head 1. The central portion 4 includes to this end two mutually opposing planar sides 5, each of which includes a window 6 formed from transparent film material.

The measuring head 1 includes a central aperture 7 which extends from one side of the measuring head so as to enable the measuring head to be pushed over the central portion 4 of the adapter. To this end, the aperture is provided with two mutually opposing, generally planar and mutual parallel surfaces 8 that face inwardly towards the aperture. Respective planar surfaces 8 on the measuring head 1 are provided with a light transmitter 9 and a light receiver 10 for transmitting and receiving infrared light respectively. The planar surfaces 8 on the measuring head 1 and the planar sides 5 of the central portion 4 of the adapter 1 are mutually designed and dimensioned so that the measuring head 1 will be positioned precisely when mounted on the adapter 2, such that light emitted by the light transmitter 9 is able to pass straight through the central portion 5 of the adapter and through its window 6, and reach the light receiver 10 without being influenced by anything other than that which passes through the interior of the central portion 4 of the adapter.

The central aperture 7 may also include a fuel cell 18 for measuring the oxygen gas content of the expiration air. To this end, a connection 17 to which such a fuel cell 18 can be connected is provided in communication with one side wall of the central portion 4 that contains no window 6.

An arrangement of the aforesaid kind that includes means for moisturising the respiratory gases and preventing contamination of the measuring devices is described in Applicant's earlier International Patent Applications PCT/SE02/01526, PCT/SE02/01527 and PCT/SE02/01528.

The measuring head is the subject of the present invention and includes on one side of the central aperture 7 a light transmitter 9, namely an IR-emitter 12, and an emitter card or board 13 which includes a microprocessor and an A/D-converter. The IR-emitter 12 is adapted to send broadband IR-radiation that is allowed to pass first through the nearest window in the adapter 2 and then through the gas sample passing through the adapter interior, whereafter the light passes through the opposite window 6 and reaches the receiver 10.

The receiver 10 includes a detector card 14 which, in turn, includes a preamplifier and a motor drive. The detector card, or board, 14 also carries a motor 15 which has a rotatable output shaft that, in turn, carries a rotatable filter wheel 16. The filter wheel 16 is situated in the measuring head 1 so as to lie nearest the window 6 through which the IR-radiation emitted by the IR-emitter 12 leaves the adapter 2, so that the IR-radiation will pass the filter wheel 16 on its way to the detector card 14. The rotatable filter wheel 16 is provided with optical band-pass filters in numbers adapted to the substances to be analysed, and also with one or more band-pass filters intended for determining the reference intensity of the IR-radiation. The detector intended to receive the IR-radiation is thus situated on the detector card 14, which also conveniently includes a preamplifier for the obtained signal values, as mentioned above.

Figure 2:
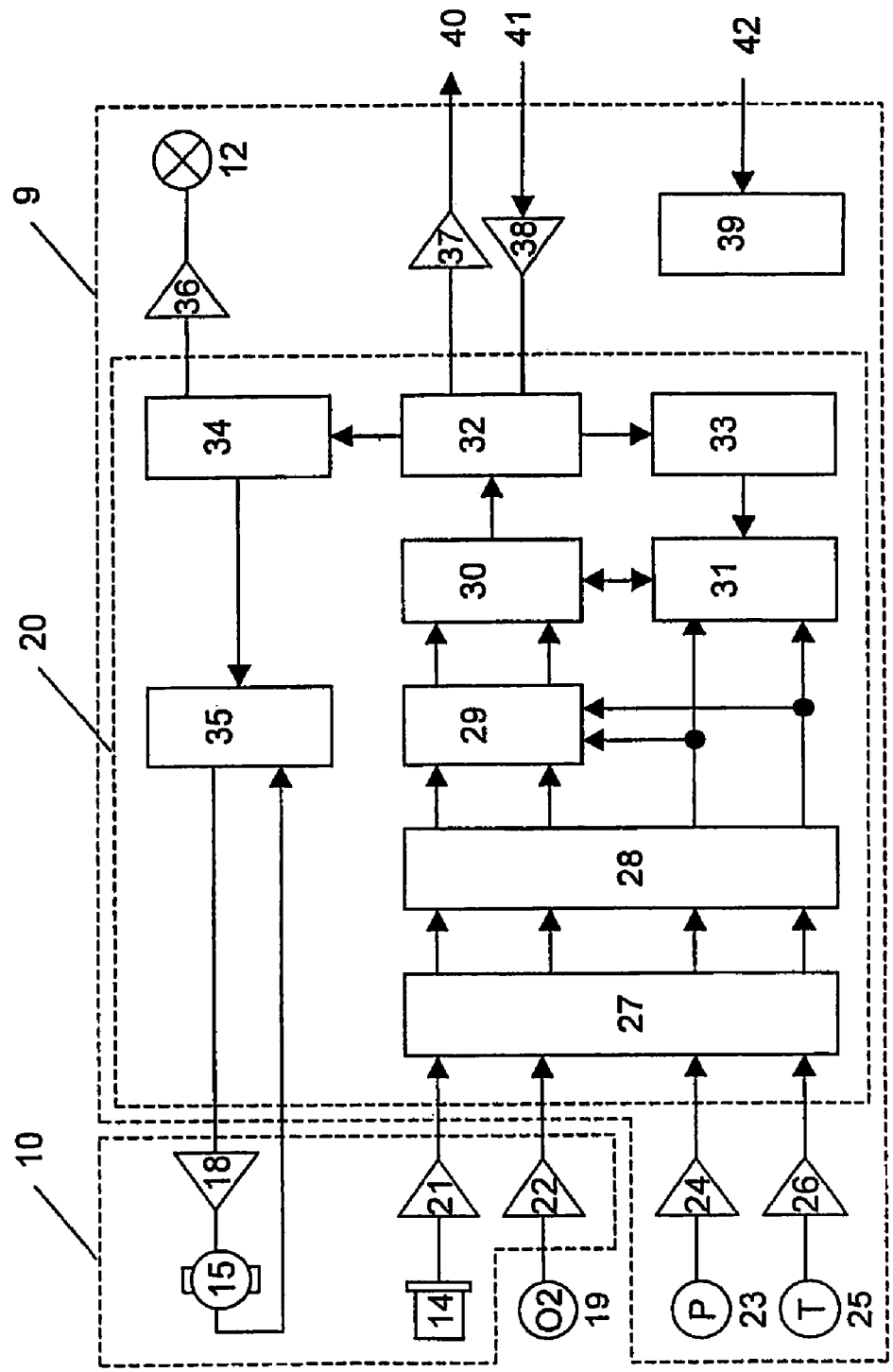
FIG. 2 is a schematically illustrated block diagram showing the measuring circuits and signal processing circuits included in the measuring head.

The measuring head also includes a signal processing unit 20, shown in the form of a block diagram in FIG. 2. The unit is comprised of a microprocessor, a built-in analogue to digital converter 27, and a calibration memory 31. In order to enable the signal processing unit 20 and all other necessary functions to be incorporated in the measuring head 1, the components used are greatly miniaturised and as many functions as possible are implemented in the processor's software.

The digital signal 40 which leaves the measuring head 1, and which is led to a presentation unit via a signal cable 11, contains gas data that has been already processed (current concentrations, inspired and expired concentrations, breathing frequency, etc. diagnostic data) for direct presentation on the presentation unit of the values system. Together with a digital input 41 for controlling the analyser (e.g. when calibrating) and a power supply line 42, these signals constitute the only connection with the values system (designated in combination the signal cable 11). The signal processing unit 20 is powered via the power supply line 42 and the requisite power is supplied to the other units in the measuring head via a voltage regulator 39. It can be mentioned within parentheses that the signals 40 and 41 are adapted electrically to RS232-levels in the drive circuit 37 and the receiver circuit 38 respectively, to suit those signal levels that occur generally on the majority of personal computers and monitoring instruments with the possibility of asynchronous series communication.

The indicator in the measuring head includes four sensors: The detector card 14, the oxygen gas sensor 19, an ambient pressure sensor 23 and a system temperature sensor 25. The signals emitted by the sensors are adapted and amplified in amplifier stages 21, 22, 24 and 26 respectively and then digitally converted in the A/D-converter 27. The signal from the detector card is demultiplexed in the unit 28, so as to obtain the current light intensity at the different wavelengths of the filter wheel. The detector signals, the oxygen gas signals, the pressure signals and the temperature signals are all filtered digitally in the unit 28 so as to suppress the inherent noise of the sensors and the amplifying stages. The detector signals and the oxygen-gas signals are compensated in the unit 29 for variations in system temperature and ambient pressure. The true gas concentrations are determined by the calculating unit 30 from the signal-processed sensor signals (compensation for such effects as spectral overlapping, non-linearities, etc. are carried out here, among other things) and from calibration data that has been saved in the non-volatile memory 31. Also determined in the calculating unit 30 are such secondary parameters as inspiratory and expiratory concentrations (the extreme values of the currently determined concentration curves) and the patient's breathing frequency calculated from the time between two successive maximums in the calculated current carbon dioxide curve. The unit for communication with the values system 32 converts calculated concentrations and secondary parameters in series in accordance with a general protocol for transfer to the values system. The unit 32 also converts series data from the values system and interprets the data as different control commands to the sensor. This enables the values system to control indirectly the unit that includes the calibration function 33 of the sensor and the control unit 34 that activates the drive stage 36 of the IR-emitter and the filter wheel speed servo 35.

The IR-analyser in the measuring head 1 is suitably of the time-multiplexed type. As mentioned earlier, the necessary control functions, e.g. the function that controls the filter wheel speed servo 35, are conveniently fully implemented in software. This also applies to the implementation of the measuring functions, e.g. the unit for demultiplexing and filtering of the detector signal 28, and the unit for temperature and pressure compensation of the detector and oxygen gas signal 29, these functions being implemented fully in software.

The described construction of a measuring head thus enables all measuring functions, evaluation functions and calculating functions to be implemented in the measuring head itself, and also enables signals to be led by the signal cable 11 to, e.g., personal computers for presentation, storage and possibly for further processing. The provision of separate bench instruments or further similar separate electronics is therefore unnecessary. The measuring head is small, inexpensive and energy-lean, and can be switched freely between different values-systems in the absence of separate calibration systems or calibration procedures.

The invention claimed is:

1. A measuring head for the analysis of gasses present in a patient's breath, the measuring head adapted for placement in close proximity to the patient's mouth, comprising:
   a central aperture (7) connecting to a central portion (4) of a breath sampling adapter (2), the breath sampling adapter adapted for placement in close proximity to the patient's mouth to obtain a sampled breath from the patient's mouth;
   two mutually opposing surfaces (8) facing inwardly towards the aperture;
   a light transmitter (9) aligned with a light receiver (10) for transmitting and receiving infrared light respectively mounting on respective ones of the two opposing surfaces (8) such that light emitted by the light transmitter passes through the central portion of the adapter and the sampled breath to reach the light receiver;
   a connection for a fuel cell measuring an oxygen gas content of the sampled breath, the connection located proximate the central aperture and in communication with the sampled breath;
   a light transmitter board (13) connected to the light transmitter, the transmitter board including a microprocessor and an A/D-converter;
   a detector board (14), connected to the light receiver, comprising a motor drive with a rotatable output shaft;
   a rotatable filter wheel (16), comprising optical band-pass filters, carried on the shaft and situated so as to lie in an optical path between the light transmitter and the light receiver so that the infrared light will pass optical band-pass filters of the filter wheel prior to arriving at the light receiver to provide a detector board output signal based on the light passing through the optical band-pass filters; and
   a signal processing unit (20) operatively connected to the light transmitter board and the detector board output signal, the signal processing unit comprising a microprocessor, an analogue to digital converter processing the detector board output signal, and a calibration data memory (31), the signal processing unit outputting a digital signal (40) containing processed gas data of the multiple gasses present in the sampled breath for direct presentation on a presentation unit of a values system.

2. The measuring head of claim 1,
   the light transmitter and light receiver are aligned so that the light emitted by the light transmitter passes straight through the central portion of the adapter to reach the light receiver.

3. The measuring head of claim 1, further comprising:
   a digital input (41) to the signal processing unit for controlling calibration,
   an oxygen gas sensor (19), an ambient pressure sensor (23), and a system temperature sensor (25) connected to the signal processing unit via the analogue to digital converter.

4. The measuring head of claim 3, further comprising:
   a demultiplexer (28) connected to an output side of the A/D-converter, the demultiplexer processing the output of the detector board to obtain the current light intensity at different wavelengths of the filter wheel, the oxygen gas sensor signal, the ambient pressure sensor signal and the system temperature signal to filter digitally to suppress sensor noise.

5. The measuring head of claim 4, wherein, an output of the demultiplexer provides system temperature compensation for the detector board output signal in a compensation unit (29).

6. The measuring head of claim 5, wherein, another output of the demultiplexer provides ambient pressure compensation for the detector board output signal in the compensation unit (29).

7. The measuring head of claim 5,
   outputs of the demultiplexer, the compensation unit, and the calibration data memory are connected as inputs to a calculating unit (30) to calculate true gas concentrations of the sampled breath.

8. The measuring head of claim 7, wherein the calibration data memory is nonvolatile memory and the calculating unit further calculates inspiratory and expiratory concentrations and the patient's breathing frequency.

9. The measuring head of claim 7, wherein, output from the calculating unit provides input to the calibration data memory.

10. The measuring head of claim 7, wherein, output from the calculating unit provides input to control a drive stage (36) of the IR-emitter and the drive motor.

11. A measuring head for the analysis of gasses present in a patient's breath, the measuring head adapted for placement in close proximity to the patient's mouth, comprising:
    a central aperture (7) adapted for placement in close proximity to the patient's mouth and sampling breath from the patient's mouth;
    a light transmitter (9) and a light receiver (10) for transmitting and receiving infrared light respectively such that light emitted by the light transmitter passes through the sampled breath to reach the light receiver;
    a connection for a fuel cell for measuring an oxygen gas content of the sampled breath;
    a light transmitter board (13) connected to the light transmitter, the transmitter board including a microprocessor and an A/D-converter;
    a detector board (14), connected to the light receiver, comprising a motor drive with a rotatable output shaft;
    a rotatable filter wheel (16), comprising optical band-pass filters, carried on the shaft and situated so as to lie in an optical path between the light transmitter and the light receiver so that the infrared light will pass optical band-pass filters of the filter wheel prior to arriving at the light receiver to provide a detector board output signal based on the light passing through the optical band-pass filters; and a signal processing unit (20) operatively connected to the light transmitter board and the detector board output signal, the signal processing unit comprising a microprocessor, an analogue to digital converter processing the detector board output signal, and a calibration data memory (31), the signal processing unit outputting a digital signal (40) containing processed gas data of the gasses present in the sampled breath for direct presentation on a presentation unit of a values system.

12. The measuring head unit of claim 11, further comprising:

a fuel cell in the form of an oxygen gas sensor (19) arranged at the connection for the fuel cell, the oxygen gas sensor, an ambient pressure sensor (23), and a system temperature sensor (25) connected to the signal processing unit via the analogue to digital converter;

a demultiplexer (28) connected to an output side of the A/D-converter, the demultiplexer processing the output of the detector board to obtain the current light intensity at different wavelengths of the filter wheel, the oxygen gas sensor signal, the ambient pressure sensor signal and the system temperature signal to filter digitally to suppress sensor noise, wherein, an output of the demultiplexer provides system temperature compensation for the detector board output signal in a compensation unit (29), another output of the demultiplexer provides ambient pressure compensation for the detector board output signal in the compensation unit (29), outputs of the demultiplexer, the compensation unit, and the calibration data memory are connected as inputs to a calculating unit (30) to calculate true gas concentrations of the sampled breath, the calculating unit further calculates inspiratory and expiratory concentrations and the patient's breathing frequency, and output from the calculating unit provides input to the calibration data memory and provides input to control the drive motor.

13. The measuring head unit of claim 11, further comprising a fuel cell in the form of an oxygen gas sensor (19) and located at the connection for a fuel cell.

* * * * *